United States Patent [19]
Johnson et al.

[11] Patent Number: 5,662,638
[45] Date of Patent: Sep. 2, 1997

[54] FLANGELESS SEAM FOR USE IN DISPOSABLE ARTICLES

[75] Inventors: Larry Kenneth Johnson, Pleasant Plain; Stephen Joseph Lange, Cincinnati, both of Ohio

[73] Assignee: The Procter & Gamble Company, Cincinnati, Ohio

[21] Appl. No.: 541,377

[22] Filed: Oct. 10, 1995

[51] Int. Cl.⁶ .............................. A61F 13/15; A61F 13/20
[52] U.S. Cl. .............................. 604/386; 2/275; 604/370; 604/385.1; 604/387; 604/389
[58] Field of Search .................... 604/370, 385.1, 604/386–387, 389, 393–394, 396, 401–402; 2/275

[56] References Cited

U.S. PATENT DOCUMENTS

| | | | |
|---|---|---|---|
| 2,115,368 | 4/1938 | Lustberg | 2/275 |
| 2,298,522 | 10/1942 | Waters . | |
| 2,372,632 | 3/1945 | Webb et al. | 2/275 |
| 2,494,905 | 1/1950 | Shumann . | |
| 4,205,679 | 6/1980 | Repke et al. | 604/394 |
| 4,610,681 | 9/1986 | Strohbeen et al. . | |
| 4,731,070 | 3/1988 | Koci . | |
| 4,890,763 | 1/1990 | Curiel . | |
| 4,938,753 | 7/1990 | Van Gompel et al. . | |
| 5,236,430 | 8/1993 | Bridges . | |
| 5,246,433 | 9/1993 | Hasse et al. . | |
| 5,491,846 | 2/1996 | Muller | 604/393 |
| 5,569,234 | 10/1996 | Buell et al. | 604/396 |
| 5,575,782 | 11/1996 | Hasse et al. | 604/394 |

*Primary Examiner*—P. Zuttarelli
*Attorney, Agent, or Firm*—David M. Weirich; Steven W. Miller; Jacobus C. Rasser

[57] ABSTRACT

A flangeless seam especially useful in disposable articles, such as training pants, incontinence articles and the like. The flangeless seam preferably comprises a first member and a second member; at least a portion of the second member overlaps at least a portion of the first member. The flangeless seam preferably further comprises a barrier member disposed between at least a portion of the overlapping portions of the first member and the second member forming a laminate having a seam area. A joining means is preferably disposed in at least a portion of the seam area joining at least a portion of the first member to at least a portion of the second member, the barrier member preventing at least a portion of the first member from becoming joined with at least a portion of the second member.

20 Claims, 8 Drawing Sheets

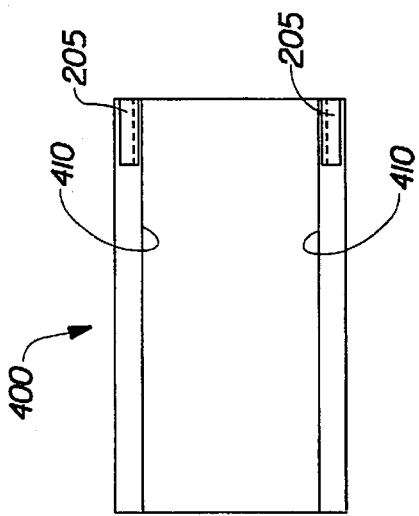
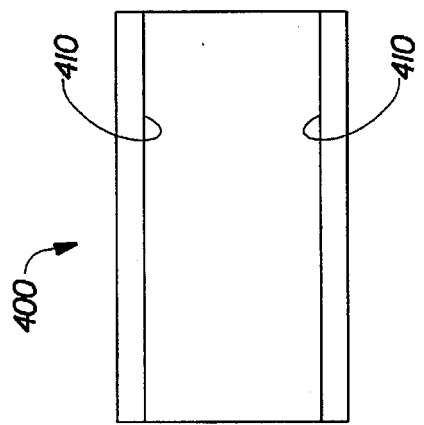
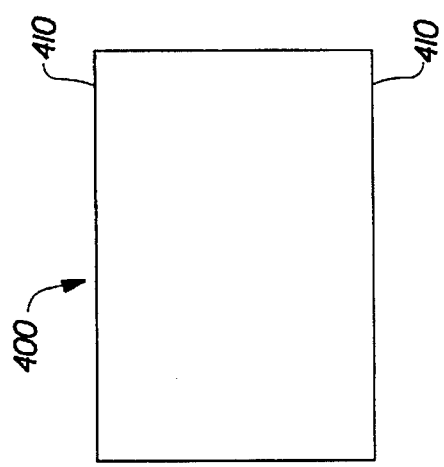
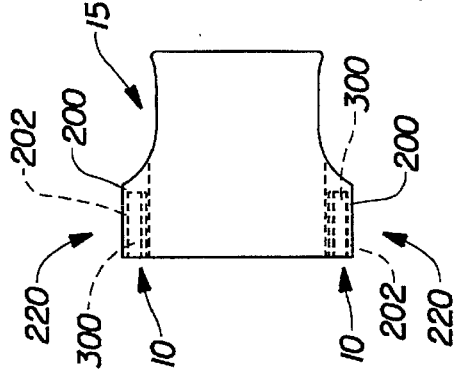
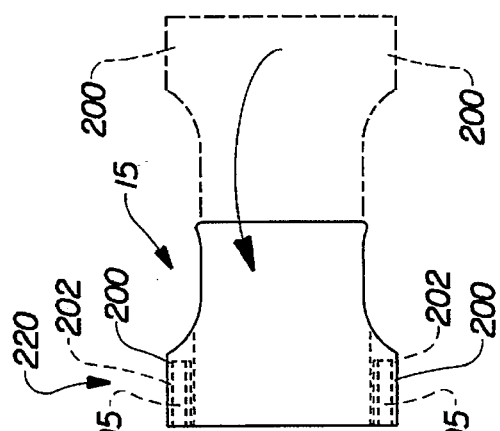
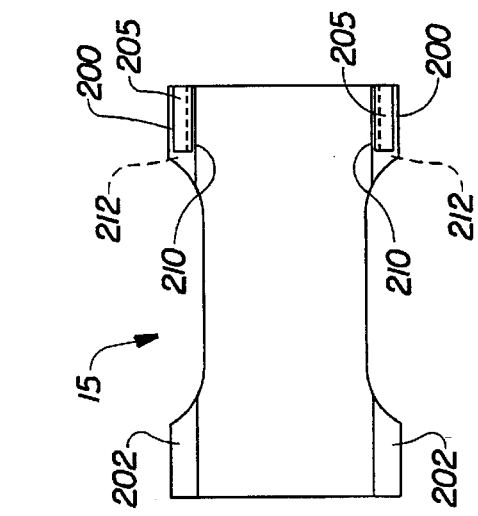

FLANGELESS SEAM FOR USE IN DISPOSABLE ARTICLES

FIELD OF THE INVENTION

The present invention relates to flangeless seams especially preferred for use in disposable, pant-like articles having at least one fixed side comprising a seam. Examples of such disposable articles include training pants, pull-on diapers or adult incontinence articles, disposable underwear for children (e.g., toddlers) or adults, and disposable parities which may be used with catamenial devices such as tampons or sanitary napkins.

BACKGROUND OF THE INVENTION

Infants and other incontinent individuals wear disposable absorbent articles to receive and contain urine and other bodily exudates. Absorbent articles having fixed sides have been popular for use in adult incontinence articles and children's toilet-training articles because it is desirable to have an absorbent article which is very garment-like in appearance and feel. (As used herein, "articles having fixed sides" refer to disposable articles such as adult incontinence briefs and training pants which are provided to the consumer in a pant-like configuration. Thus, the articles generally have the front and rear portions joined together to form a waist hoop and leg openings. This is unlike conventional diapers which are provided to the consumer with the front and rear portions unjoined.) For adults, the garment-like appearance and feel can help reduce any embarrassment associated with the use of incontinence articles. For children, especially in their toilet training stage, the garment-like feel and appearance can help the child distinguish the article, such as training pants, from a diaper and can help the child adjust to cloth undergarments.

With regard to disposable articles such as adult incontinence briefs and training pants, consumers are very conscious about the fit, containment characteristics and the overall appearance of the articles. One improvement that has become popular with consumers has been the addition of stretch or elasticity throughout different portions of the articles. One example of a commercially available disposable training pant is disclosed in U.S. Pat. No. 5,246,433 entitled "Elasticized Disposable Training Pant and Method of Making the Same", issued to Hasse et al. on Sep. 21, 1993.

Despite the improvements made to disposable articles having fixed sides, such articles generally include seams for joining the front and rear portions. The seams are often constructed by positioning the lateral edges of the front and rear portions of the article in a face-to-face relationship with one another and then gluing, sewing, heat sealing or ultrasonically sealing the edges to form flanges or fin seams. Flanges or fin seams can be unsightly if located on the outwardly facing surface of the article or irritating to the wearer if located on the inward surface. Thus, attempts have been made to reduce the outwardly or inwardly extending portions of the flanges of fin seams. However, doing so may reduce the strength of the bond between the front and rear portions of the article which may allow the seam to fail during use.

Another important aspect of a disposable article is the cost of the article. Because the article is intended to be discarded, generally after a single use, consumers are very conscious of the cost of the article. Thus, it would be advantageous to be able to provide a seam that can be constructed economically on machinery that is very similar to that already in place.

Further, it would be advantageous to reduce the amount of material that is needed to produce a satisfactory seam or that is wasted in attempting to make the seam preferable to the consumer.

Therefore, it is an object of the present invention to provide flangeless seams especially suited for use in disposable articles, such as disposable training pants, adult incontinence briefs and the like which are discrete, strong and economical to manufacture.

It is another object of the present invention to provide flangeless side seams which can be produced more quickly and easily than the sewn seams of the prior art and which provide a more garment-like appearance and are less irritating than the heat-sealed, adhesively bonded or ultrasonically sealed seams of the prior art.

It is yet another object of the present invention to provide flangeless side seams which reduces the amount of material needed to produce the seam as well as the material waste associated with providing a seam that is acceptable to the consumer.

It is a further object of the present invention to provide a disposable article, such as disposable training pants, having flangeless seams.

SUMMARY OF THE INVENTION

According to the present invention, a flangeless seam especially useful in disposable articles, such as training pants, incontinence articles and the like is provided. The flangeless seam preferably comprises a first member and a second member, wherein at least a portion of the second member overlaps at least a portion of the first member. The flangeless seam preferably further comprises a barrier member disposed between at least a portion of the overlapping portions of the first member and the second member forming a laminate having a seam area. A joining means is preferably disposed in at least a portion of the seam area joining at least a portion of the first member to at least a portion of the second member, the barrier member preventing at least a portion of the first member from becoming joined with at least a portion of the second member.

Alternatively, the flangeless seam may comprise a first member; a second member; a barrier member having a first portion and a second portion separated by a fold, the first portion of the barrier member being juxtaposed with at least a part of the first member and the second portion of the barrier member being juxtaposed at least a part of the second member forming a laminate. The flangeless seam preferably further includes a joining means disposed across at least a part of the laminate, at least a part of the first potion of the barrier member being joined with at least a part of the first member and at least a part of the second portion of the barrier member being joined with at least a part of the second member, wherein the first portion of the barrier member and the second portion of the barrier member are not joined such that the unjoined first and second portions may be separated to provide the seam in its open configuration.

While the flangeless seams of the present invention may be used in any disposable article, a preferred disposable article comprises an elasticized waistband, elasticized leg cuffs and an absorbent assembly comprising a backsheet, topsheet, and absorbent core.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

FIGS. 12A–G are schematic views of a parts one method for making one embodiment of the seams of the present invention.

DETAILED DESCRIPTION OF THE INVENTION

Figure 1:
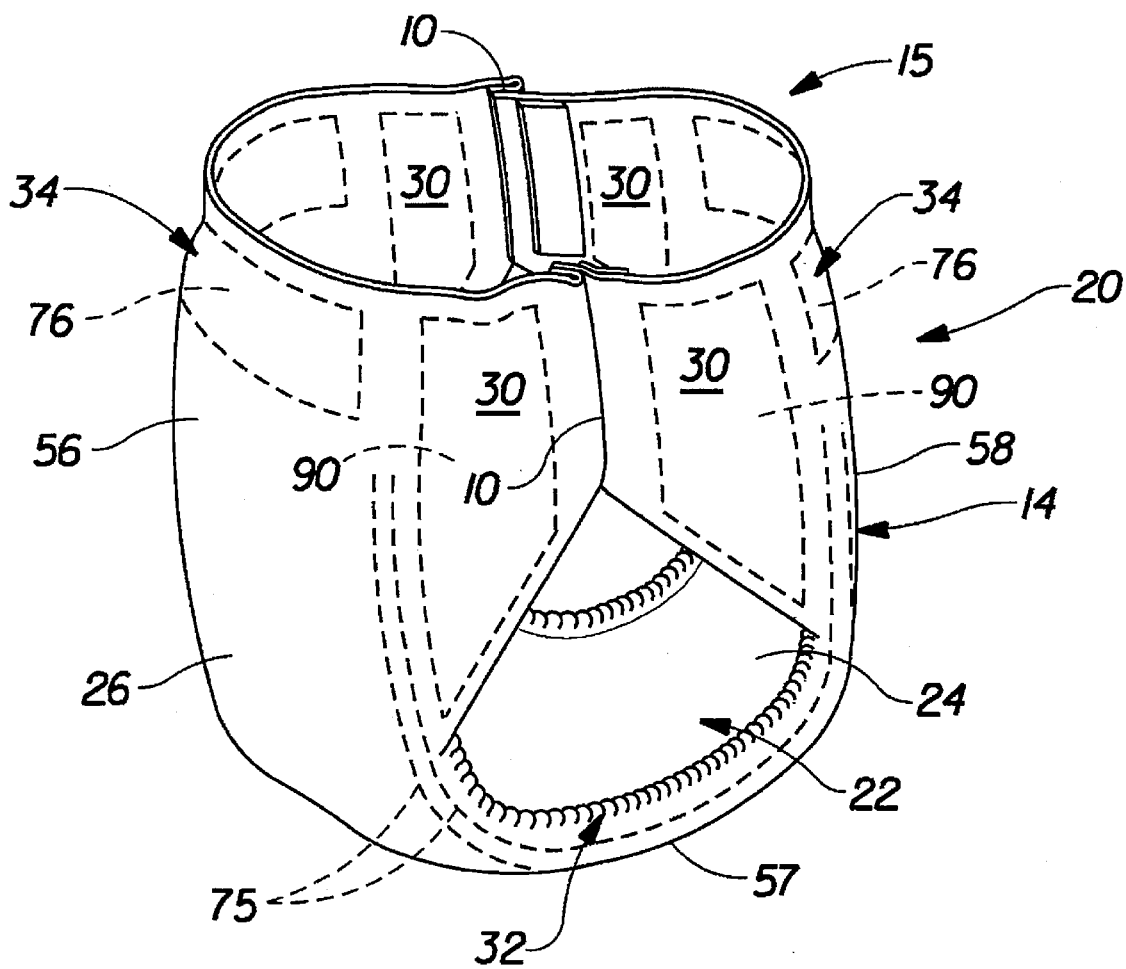
FIG. 1 is a perspective view of a disposal training pant embodiment of the present invention in a typical in-use configuration as it would be applied to a wearer.

Referring to the drawings, it will be noted that FIG. 1 is a perspective view of a disposable garment 15. A disposable garment is one which is intended to be discarded after it is used (i.e., it is not intended to be laundered or otherwise restored or reused). The disposable garment 15 may be provided with an absorbent assembly which is placed in close proximity to the body of the wearer to absorb and contain the various exudates discharged from the body. A preferred embodiment of the disposable garment 15 of the present invention, disposable training pants 20, is shown in FIG. 1. Examples of other suitable training pants, as well as preferred components and alternative embodiments, in which the flangeless seams of the present invention may be used can be found in U.S. Pat. Nos. 5,236,430 entitled "Disposable Training Pant Having Fusion-Slit Side Seams", issued to Russell P. Bridges on Aug. 17, 1993, and 5,246,433 entitled "Elasticized Disposable Training Pant and Method of Making the Same", issued to Hasse et al. on Sep. 21, 1993. The specification, claims and drawings of each of these patents are hereby incorporated by reference herein.

The training pants 20 of FIG. 1, preferably comprise a chassis 14, an absorbent assembly 22, and at least one flangeless seam 10. (As used herein the term "flangeless seam" refers to a seam which extends from the disposable training pants 20 about $1/8$ inch or less. Preferably the flangeless seam will extend from the article about $1/16$ inch or less, and more preferably $1/32$ inch or less.) The chassis 14 of the present invention preferably has a symmetric, modified hour-glass shape. The chassis 14 preferably comprises a front portion 56, a rear portion 58, a crotch portion 57. The chassis 14 preferably further comprises elasticized leg cuffs 32, an elasticized waistband 34, elasticized side panels 30 and longitudinal side regions 88 (shown in FIG. 2). The longitudinal side regions 88 preferably comprise a polymeric material to facilitate the seaming process which is described in greater detail below.

Figure 2:
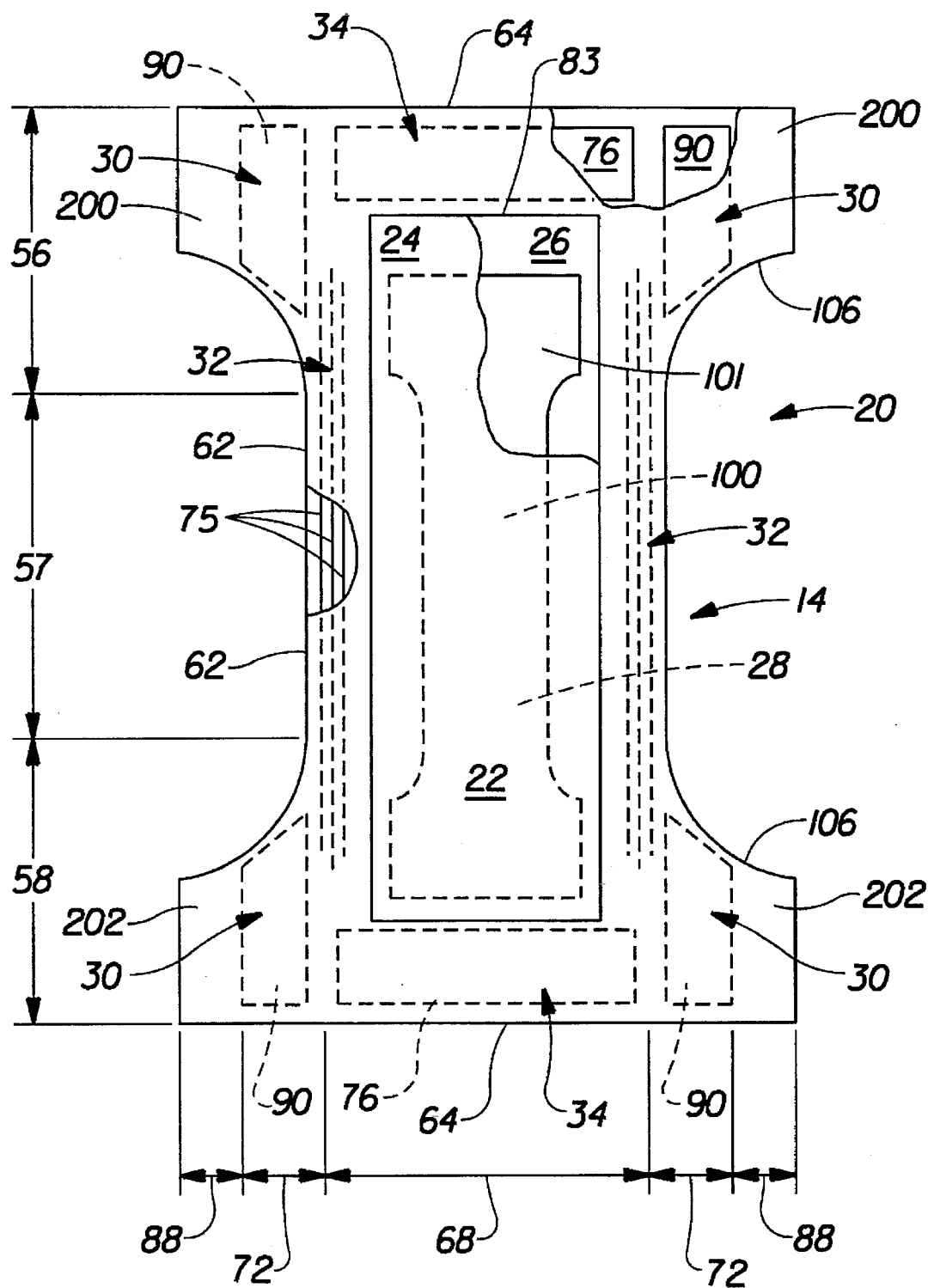
FIG. 2 is a plan view of the chassis of a training pant embodiment of the present invention having portions cut away to reveal the underlying structure, the surface which will form the outer surface of the disposable article facing away from the viewer.

FIG. 2 is a partially cut-away perspective view of the disposable garment 20 of FIG. 1, prior to the front portion 56 and rear portion 58 of the chassis 14 being joined together. (As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.)

The chassis 14 of the present invention preferably has a symmetric, modified hour-glass shape. The chassis 14 will have at least a front portion 56, a rear portion 58, a crotch portion 57, and longitudinal side regions 88, and will comprise a polymeric material in at least the longitudinal side regions 88 to facilitate the seaming process which will be described in greater detail herein below. Further, as shown in FIG. 2, a preferred embodiment of the chassis 14 will comprise an absorbent assembly 22. The absorbent assembly 22 of the disposable training pants 20 may be integral with the training pants 20 or may be an insert, i.e. an element formed separately from the chassis and inserted therein.

As shown in FIG. 2, the absorbent assembly 22 of the disposable training pants 20 preferably comprises at least an absorbent core 28 and an outer covering layer comprising a topsheet 24 and a backsheet 26. The absorbent core 28 preferably has a garment surface 100 and a body surface 101. The absorbent core 28 may be any absorbent means which is generally compressible, conformable, nonirritating to the wearer's skin, and capable of absorbing and retaining liquids such as urine and other certain body exudates.

The absorbent core 28 may be manufactured in a wide variety of sized and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulosic fibers, tissue including tissue wraps, absorbent foams, absorbent sponges, superabsorbent polymers, absorbent gelling materials, or any equivalent material or combinations of materials. The configuration and construction of the absorbent core may also be varied (e.g., the absorbent core may have varying caliper zones a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the disposable garment 20. Further, the size and absorbent capacity of the absorbent core 28 may be varied to accommodate wearers ranging from infants through adults.

A preferred embodiment of the absorbent assembly 22 has a symmetric, modified hour-glass shape absorbent core 28. While a preferred embodiment of the absorbent assembly 22 has a modified hourglass-shaped absorbent core 28, it should be understood that the size, shape, configuration and total absorbent capacity of the absorbent core 28 may be varied to accommodate wearers ranging from infants to adults. Therefore, the dimensions, shape and configuration of the absorbent core may be varied (e.g., the absorbent core may have a varying caliper, or a hydrophilic radiant, or may or may not contain absorbent gelling materials). An exemplary absorbent structure for use as the absorbent core 28 of the present invention that has achieved wide acceptance and commercial success is described in U.S. Pat. No. 4,610,678 entitled "High-Density Absorbent Structures" issued to Weisman and Goldman on Sep. 9, 1986; U.S. Pat. No. 4,673,402 entitled "Absorbent Articles With Dual-Layered Cores" issued to Weisman, Houghton, and Gellert on Jun. 16, 1987; and U.S. Pat. No. 4,888,231 entitled "Absorbent Core Having A Dusting Layer" issued to Angstadt on Dec. 19, 1989; also describe absorbent structures that are useful in the present invention. Each of these references are incorporated herein by reference.

The backsheet 26 is positioned adjacent the garment surface 100 of the absorbent core 28 and is preferably joined thereto by attachment means such as those well known in the art. For example, the backsheet 26 may be secured to the absorbent core 28 by a uniform continuous layer of adhesive, a patterned layer of s adhesive, or an array of separate lines, spirals, or spots of adhesive. Adhesives which have been found to be satisfactory are manufactured by Century Adhesives, Inc. of Columbus, Ohio and marketed as Century 5227; and by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combination of these attachment means as are known in the art.

The backsheet 26 is impervious to liquids (e.g. urine) and is preferably manufactured from a thin plastic film, although other flexible liquid impervious material may also be used. As used herein, the term "flexible" refers to materials which are compliant and will readily conform to the general shape and contours of the human body. The backsheet 26 prevents the exudates absorbed and contained in the absorbent core 28 from wetting articles which contact the disposable training pants 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a film having a thickness of from about 0.012 mm (0.5 mil) to about 0.051 mm (2.0 mils).

The size of the backsheet 26 is dictated by the size of the absorbent core 28 and the exact disposable garment design selected. In a preferred embodiment, the backsheet 26 will wrap around at least the absorbent core and possibly over the edge portions of the topsheet 24 in at least the crotch portion 57, so that the elasticized leg cuff 32 will be free from any backsheet material, and thus, are not inhibited by the backsheet material. Alternatively, the topsheet 24 may wrap around the core and under the edge portions of the backsheet 26 in at least the crotch portion 57, or the topsheet 24 and backsheet 26 may be "side-notched" in the crotch portion 57 so that the elasticized leg cuffs 32 are not inhibited by the backsheet material.

The topsheet 24 is positioned adjacent the body surface 101 of the absorbent core 28 and is preferably joined thereto and to the backsheet 26 by attachment means such as those well known in the art. Suitable attachment means are described with respect to joining the backsheet 26 to the absorbent core 28. In a preferred embodiment of the present invention, the topsheet 24 and the backsheet 26 are joined directly to each other in the areas extending beyond the absorbent core 28 and are indirectly joined together by directly joining them to the absorbent core 28 by the attachment means.

The topsheet 24 is compliant, soft feeling, and nonirritating to the wearer's skin. Further, the topsheet 24 is liquid pervious permitting liquids (e.g. urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of hydrophilic material comprising about 20% to 30% rayon so as to feel wet and signal a discharge of urine to a toilet training child.

There are a number of manufacturing techniques which may be used to manufacture the topsheet 24. For example, the topsheet 24 may be a nonwoven web of fibers. When the topsheet comprises a nonwoven web, the web may be spunbonded, carded, wet-laid, meltblown, hydroentangled, combinations of the above, or the like. A preferred topsheet is carded and thermally bonded by means well known to those skilled in the fabrics art. A suitable topsheet is manufactured by Fiberweb North America and available as 80/20 polypropylene/rayon carded thermally bonded nonwoven.

In a preferred embodiment of the present invention, at least a portion of the topsheet 24 and the backsheet 26 will be subjected to mechanical stretching in order to provide a "zero strain" stretch laminate that forms the elasticized side panels 30. Thus, the topsheet 24 and the backsheet 26 are preferably elongatable, most preferably drawable, but not necessarily elastomeric, so that they will, upon mechanical stretching, be at least to a degree permanently elongated such that they will not fully return to then original undistorted configuration. In preferred embodiments, the topsheet 24 and the backsheet 26 can be subjected to mechanical stretching without undue rupturing or tearing. Thus, it is preferred that the topsheet 24 and the backsheet 26 have a low cross-machine direction (lateral direction) yield strength.

Examples of such "zero strain" stretch laminates are disclosed in U.S. Pat. No. 2,075,189 issued to Galligan, et al. on Mar. 30, 1937; U.S. Pat. No. 3,025,199 issued to Harwood on Mar. 13, 1962; U.S. Pat. No. 4,107,364 issued to Sisson on Aug. 15, 1978; U.S. Pat. No. 4,209,563 issued to Sisson on Jun. 24, 1980; U.S. Pat. No. 4,834,741 issued to Sabee on May 30, 1989; and U.S. Pat. No. 5,151,092 issued to Buell et al., on Sep. 29, 1992. All of the above referenced patents are hereby incorporated by reference.

Alternatively, the topsheet and backsheet 24 and 26, portions thereof or any other element of the disposable article 20 may comprise a structural elastic-like film (SELF) web. A structural elastic-like film web is an extensible material that exhibits an elastic-like behavior in the direction of elongation without the use of added elastic materials. SELF webs suitable for the present invention are more completely described in the co-pending, commonly assigned U.S. patent application Ser. No. 08/203,456 entitled "Absorbent Article with Multiple Zone Structural Elastic-Like Film Web Extensible Waist Feature" filed by Donald C. Roe, et al. on Feb. 24, 1994, and International Application WO 9503765, entitled "Web Materials Exhibiting Elastic-Like Behavior" published Feb. 9, 1995, in the names of Chappell et al., both of which are incorporated herein by reference.

Particularly preferred methods and apparatus used for making "zero strain" stretch laminates out of the inner cover, outer cover, and an elastomeric member positioned between the same, use meshing corrugated rolls to mechanically stretch the components. A discussion of suitable apparatus and methods for mechanically stretching portions of a diaper is contained in the hereinbefore referenced U.S. Pat. No. 4,107,364 issued to Sisson on Aug. 15, 1978 and U.S. Pat. No. 4,834,741 issued to Sabee on May 30, 1989. Particularly preferred apparatus and methods are disclosed in U.S. Pat. No. 5,167,897 issued to Weber et al. on Dec. 1, 1992; U.S. Pat. No. 5,156,793 issued to Buell et al. on Oct. 20, 1992; and U.S. Pat. No. 5,143,679 issued to Weber et al. on Sep. 1, 1992; the specifications and drawings of which each are incorporated herein by reference.

The disposable training pants 20 preferably further comprise elasticized leg cuffs 32 for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 entitled "Contractible Side Portions For a Disposable Diaper" issued to Buell on Jan. 14, 1975, describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz and Blaney on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinent garment having side-edge-leakage-guard gutters configured to contain free liquids within the garment. Each of these patents are incorporated herein by reference. While each elasticized leg cuff 32 may be configured so as to be similar to any of the leg bands, side flaps, barrier cuffs, or elastic cuffs described above, it is preferred that each elasticized leg cuff 32 comprise one or more elastic strands 75.

The disposable training pants 20 preferably further comprise an elasticized waistband 34 disposed adjacent the end edge 64 of the disposable training pants 20 in at least the rear portion 58, and more preferably, has an elasticized waistband 34 disposed in both the front portion 56 and the rear portion 58. (As used herein, the term "disposed" is used to mean that an element(s) of the disposable garment is formed (joined and positioned) in a particular place or position as an unitary structure with other elements of the disposable garment or as a separate element joined to another element of the disposable garment.)

The waistband of the disposable training pants 20 is that portion which is intended to be placed adjacent the wearer's waist. The elasticized waistband 34 provides a member that maintains a defined area coverage, contacts the wearer's waist, and is elastically extensible in at least the lateral direction so as to dynamically fit against the waist of the wearer and to dynamically conform to the waist of the wearer so as to provide improved fit. Thus, the waistband is generally that portion of the disposable training pants 20 extending from the end edge 64 of the disposable training pants 20 to at least the waist edge 83 of the absorbent core 28. While the elasticized waistband 34 can comprise a separate element affixed to the chassis 14 of the disposable training pants 20, the waistband is preferably an extension of other elements of the disposable training pants 20 such as the topsheet 24, the backsheet 26, or any combination of these elements and an elastomeric material joined thereto.

Disposable training pants are often constructed so as to have two elasticized waistbands; one positioned in the front portion 56 and one positioned in the rear portion 58. The disposable training pants 20 at least has an elasticized waistband 34 disposed in at least the central region 68 of the rear portion 58. Preferably, as shown in FIG. 2, another elasticized waistband 34 is disposed in the front portion 56. Preferably both elasticized waistbands 34 are disposed between the elasticized side panels 30.

The elasticized waistband 34 may be constructed in a number of different configurations including those described herein with regard to the elasticized side panels 30. In a preferred embodiment of the present invention shown in FIG. 2, the elasticized waistband 34 comprises an elastic waistband member 76 interposed between the topsheet 24 and the backsheet 26 and operatively associated with either or both the topsheet 24 or the backsheet 26 to gather the front portion 56 and rear portion 58 of the disposable training pants 20. An example of such an elasticized waistband for use herein is the elasticized waistband disclosed in U.S. Pat. No. 4,515,595 entitled "Disposable Diapers With Elastically Contractible Waistbands", which issued to Kievit and Osterhage on May 7, 1985, and which patent is incorporated herein by reference.

Any suitable elastomeric material as known in the art may be used as the elastic waistband member 76 of the present invention. Examples of suitable elastomeric materials include elastomeric films, elastomeric foams such as polyurethane foams or crosslinked natural rubber foams; formed elastic scrim; elastomeric films such as heat shrinkable elastic materials; elastomeric film laminates such as a laminate of a heat-shrinkable elastomeric film and a resilient member; elastomeric stretch laminates such as "zero strain" stretch laminates as described hereinbefore or mechanically stretched pretensioned stretch laminates and elastic strands made from rubber, LYCRA, or other materials. In a preferred embodiment, the elastic waistband member 76 comprises a heat shrinkable elastomeric film.

In an alternative embodiment, the elasticized waistbands 34 and the elasticized side panels 30 can be formed by securing a single piece of elastomeric material to the disposable training pants 20 in both the side panels 72 and the central region 68 of the rear portion 58 and securing a single piece of elastomeric material to the disposable training pants 20 in both the side panels 72 and central region 68 of the front portion 56. Thus, the elasticized waistband 34 and the elasticized side panels 30 can be formed from the same piece of material to form a unitary structure.

In a preferred embodiment, the disposable garment also comprises elasticized side panels 30 disposed in the front portion 56 and rear portion 58. The elasticized side panels 30 provide an elastically extensible feature that provides a more comfortable and contouring fit by initially conformably fitting the disposable garment to the wearer and sustaining this fit throughout the time of wear well past when the disposable garment has been loaded with exudates since the elasticized side panels allow the sides of the disposable garment to expand and contract. While the disposable training pants 20 of the present invention preferably has the elasticized side panels 30 disposed in both the front portion 56 and rear portion 58; alternatively, the disposable training pants 20 may be provided with elasticized side panels 30 disposed in the front portion 56 only or in the rear portion 58 only.

The elasticized side panels 30 of the disposable training pants 20 may be constructed in a number of configurations. The elasticized side panels 30 of the present invention may be unitary or integral with the chassis 14 or may comprise a separate elastically extensible material or laminate joined to the chassis 14. As shown in FIGS. 1 and 2, each elasticized side panel 30 preferably comprises an elastic side panel member 90 operatively associated therewith. Examples of a disposable articles with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and U.S. Pat. No. 5,246,433 issued to Hasse et al., on Sep. 21, 1993. Each of these patents is hereby incorporated by reference herein.

As shown in FIG. 2, each side panel 72 preferably comprises that portion of the chassis 14 that extends laterally outwardly from and along the central region 68 of the chassis 14 to the longitudinal side region 88 of the chassis 14. The side panel 72 generally extends longitudinally from the end edge 64 of the chassis 14 to the portions of the longitudinal edge 62 of the chassis 14 that forms the leg opening (this segment of the longitudinal edge 62 being designated as leg edge 106). In a preferred embodiment of the present invention, each side panel 72 is formed by the portions of the topsheet 24 and the backsheet 26 that extend beyond the central region 68 of the chassis 14.

Figure 8:
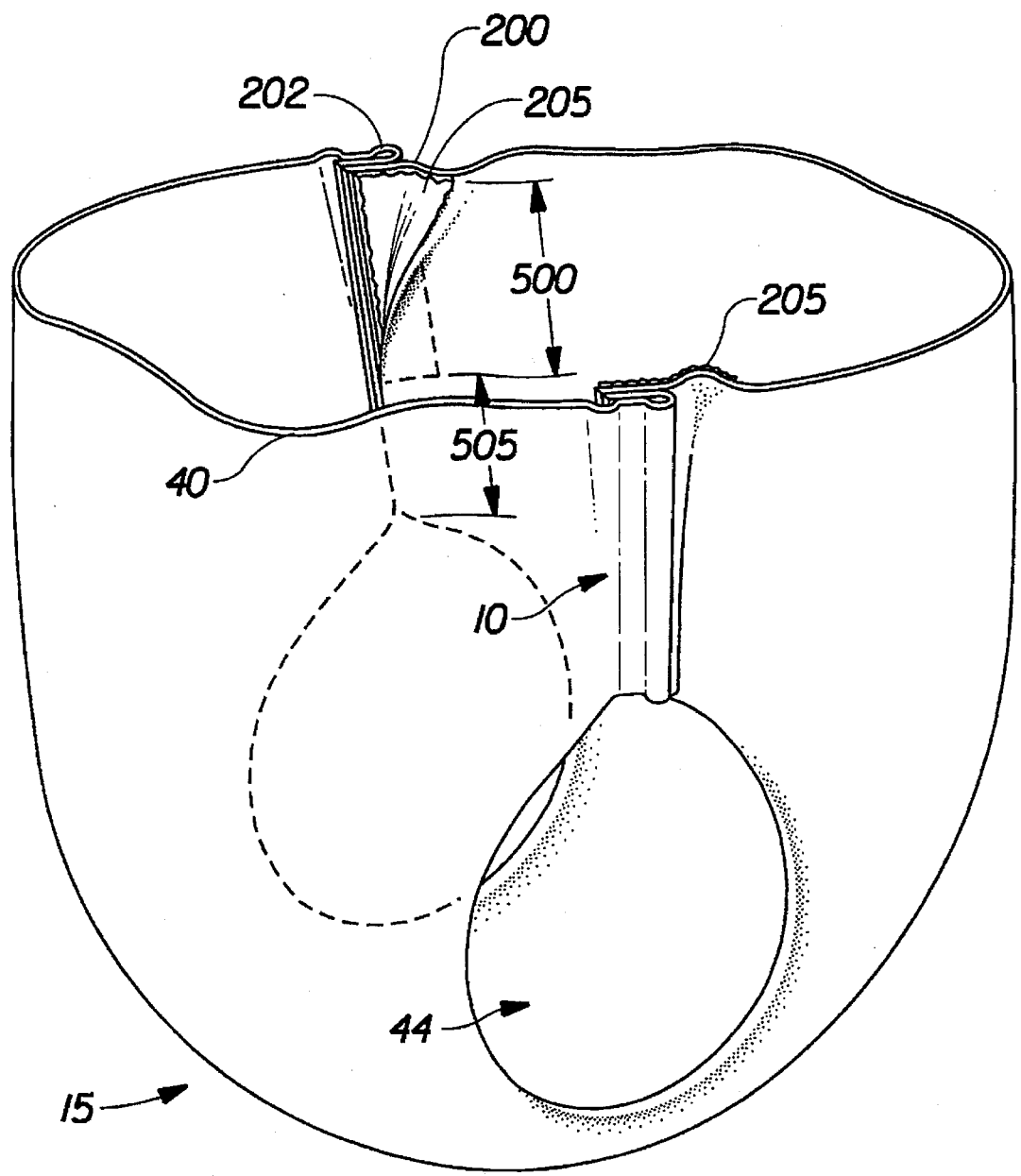
FIG. 8 is a perspective view of one preferred disposable article comprising the openable seams shown in FIGS. 5–7.

Preferably, the chassis 14 comprises at least one longitudinal side region 88 having a first member 200 and a second member 202. As shown in FIG. 2, the chassis 14 more preferably comprises a pair of opposing longitudinal side regions 88, each of which each comprise a first member 200 and a second member 202. (Although the first members 200 are shown in FIG. 2 to be disposed in the front portion 56 and the second members 202 are shown to be disposed in the rear portion 58, embodiments are contemplated wherein the first members 200 are disposed in the rear portion 58 and the second members 202 are disposed in the front portion 56.) In preferred embodiments of the present invention, at least one pair of the first and second members 200 and 202 are joined with the flangeless seams described below to form a closure that joins at least a part of the front portion 56 of the chassis 14 with at least a part of the rear portion 58 of the chassis 14. More preferably, both pairs of first and second members 200 and 202 are joined with the flangeless seams described below to form a disposable pant having a waist hoop 40 and a pair of leg openings 44. (One embodiment is shown in FIG. 8.)

The first and second members 200 and 202 may be separate members joined to the longitudinal side regions 88 or may be integral with the longitudinal side regions 88. (As used herein, the term "integral" refers to elements that are joined to one another in such a way that the elements are neither divided nor discontinuous with the other elements.) If the first and second members 200 and 202 are joined with the chassis 14, any suitable means for joining known in the art may be used. In a preferred embodiments, the first and second members 200 and 202 are extensions of the topsheet 24, the backsheet 26, both the topsheet 24 and the backsheet 26 or any other element of the disposable article that may be suitable for joining to form a flangeless seam.

The first member 200 and the second member 202 may comprise any material known in the art that is suitable for use in disposable articles such as training pants 20 which may be joined together to form the flangeless seam 10 of the present invention as described below. Preferably, the layers of material making-up the seaming area, have similar melting points. In one preferred embodiment, each layer of the seaming area will comprise 100% polypropylene fibers. Examples of other suitable materials include, but are not limited to polymeric films, woven webs, nonwoven webs, or combinations of these or other materials known in the art. Examples of preferred materials include the carded nonwoven DPN290 available from Fiberweb, Clopay 1401 polyethylene film available from the Clopay Corporation of Cincinnati, Ohio, and FS2 or Plus polyethylene films available from Tredegar Film Products, Inc., of Terre Haute Ind.

The Flangeless Seam

One embodiment of the flangeless seam 10 of the present invention comprises a first member 200 and a second member 202. Preferably at least a portion of the first member 200 overlaps at least a portion of the second member 202. The flangeless seam further comprises a barrier member 205 disposed between at least a portion of the overlapping portions of the first member 200 and the second member 202 forming a laminate 220 having a seaming area 250. A joining means 300 is preferably disposed in at least a portion of the seam area 250. Preferably, the joining means 300 joins at least a portion of the first member 200 to at least a portion of the second member 202. However, the barrier member 205 prevents at least a portion of the first member 200 from becoming joined with at least a portion of the second member 202.

Figure 3:
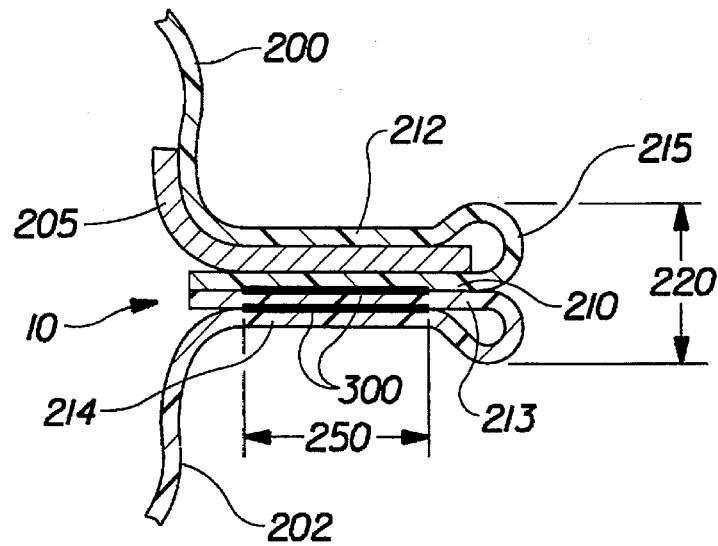
FIG. 3 is an enlarged cross-sectional view of one embodiment of the seam area in the configuration in which the seam is fixed.
Figure 4:
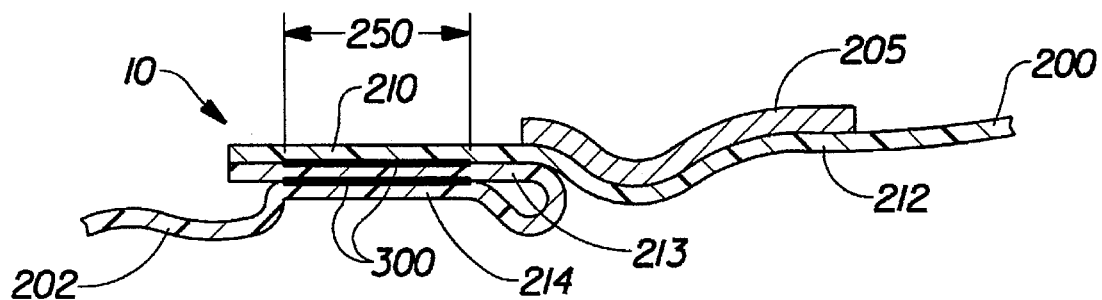
FIG. 4 is an enlarged cross-sectional view of the seam area shown in FIG. 3 in an open configuration.

A preferred embodiment of the present invention is shown in FIGS. 3 and 4. The flangeless seam 10 preferably has an open configuration and a seaming configuration. As used herein, the term "seaming configuration" refers to a configuration in which the elements of the seam 10 may positioned with regard to each other and joined to form the seam 10. (FIG. 3) The term "open configuration" refers to the configuration of the elements comprised in the seam 10 after they have been opened or placed in a configuration in which the seam 10 is likely to be used, such as in a diaper that has been placed on a wearer. (FIG. 4)

The flangeless seam 10 of the present invention preferably comprises a first member 200 having a first proximal portion 212 and a first distal portion 210. A fold 215 preferably separates the first member 200 into the proximal portion 212 and an opposing distal potion 210. The first distal portion 210 is preferably foldable upon at least a portion of the first proximal portion 212 so as to provide a common interface between the first distal potion 210 and the first proximal portion 212. The flangeless seam 10 preferably further comprises a second member 202 having a second proximal portion 214 and a second distal potion 213. The first distal portion 210 and the second distal portion 213 are preferably joinable to one another.

The lengths of the proximal portions 212 and 214 and the distal potions 210 and 213 are not critical, and each may comprise any number of layers and/or folds. In fact, it is recognized that one way to increase the strength of the finished seam is to provide more material in the seam area 250. This is especially relevant when the joining means 205 comprises some sort of heat, pressure, heat and pressure, or ultrasonic bonding wherein at least a potion of the bond comprises the material to which the joining means 300 is applied.

The flangeless seam 10 preferably further comprises a barrier member 205 disposed between at least a part of the common interface of the first distal and first proximal portions 210 and 212. Thus, when the flangeless seam 10 is in the seaming configuration (FIG. 3), a laminate 220 is formed. The laminate 220 preferably comprises at least a part of the first proximal portion 212, at least a part of the first distal portion 210, at least a part of the second distal portion 213 and at least a part of the barrier member 205.

The barrier member 205 is provided to ensure that when the flangeless seam 10 is formed, joining the first member 200 and the second member 202, at least a portion of the first member 200 is not joined with at least a portion of the second member 202. The barrier member 205 may comprise any known material or means that will prevent the first member 200 and the second member 202 from becoming fully joined when the seam is formed. For example, the barrier member 205 may be a separate element joined to the first member 200 or a separate member not joined to the first member 200, but merely provided in a position to act as a barrier while the seam is being formed. Alternatively, the barrier member 205 may comprise an element or material that is unitary or integrated with at least a portion of the first member 200, such as a material coextruded with the first member 200, or portion of the first member 200 that has been chemically, mechanically or otherwise manipulated to act as a barrier to the joining means 300 used to form the seam. It is also contemplated that the barrier member 205 may comprise a material that will be removed from the flangeless seam 10 after the joining means 300 is disposed across the seam area 250.

Examples of suitable barrier members include, but are not limited to KEVLAR, NYLON, polypropylene films, polyethylene films, scrims, woven materials or laminates of any of these or any other suitable materials known in the art. Other suitable barrier member materials may comprise silicone, talc, clay, TEFLON, lotions or any other suitable release means that will prevent predetermined portions of the barrier member 205 from becoming joined when the joining means 300 is applied. Yet other suitable barrier members comprise foams; laminates of films, foams and/or nonwoven webs; adhesives; coated or non-coated paper products; cotton and cotton-flocked films. Generally, the composition of the barrier member 205 will be limited only by the particular joining means 300 which will be used and the strength characteristics necessary to provide an acceptable seam.

The flangeless seam 10 preferably further comprises a joining means 300 spanning at least a portion of the laminate 220 in the seaming configuration (FIG. 3). The joining means 300 preferably joins at least a part of the first distal portion 210 with at least a part of the second distal portion 213. However, the barrier member 205 preferably prevents the joining means 300 from joining at least a part of the common interface of the first proximal portion 212 and the first distal portion 210 such that the unjoined parts of the first proximal portion 212 and the first distal portion 210 may be separated to provide the flangeless seam 10 in its open configuration, as shown in FIG. 4.

The joining means 300 may comprise any means suitable for joining the materials comprised in the first and second members 200 and 202. However, a joining means must be chosen that will join the desired portion or portions of the first member 200 with the desired portion or portions of the second member 202 while not joining the those portions of the first member 200 and the second member 202 which have been designated to remain unjoined. Thus, it is important to choose a joining means 300 that will work effectively with the barrier member 205 to achieve the desired results. Suitable joining means include, but are not limited to, adhesives, pressure bonding means, heat bonding means, heat and pressure bonding means, ultrasound bonding means, infrared bonding means or any other joining means or combination of joining means known in the art.

Examples of suitable adhesive joining means include, but are not limited to, hot melt adhesives such as Findley 2120, or Findley 2379 available from Findley Adhesives Corporation of Wauwatosa, Wis. Such adhesive may be applied with slot, spiral or control spray coating equipment such as those available from Nordson Corporation of Norcross, Ga. Examples of methods and apparatus for treating materials with ultrasonic energy are disclosed in U.S. Pat. No. 3,657,033 issued to Sager on Apr. 18, 1972 entitled "Method and Apparatus for Continuous Cutting and Joining of Thermoplastic Sheet Material"; U.S. Pat. No. 4,400,227 issued to Riemersma on Aug. 23, 1983; U.S. Pat. No. 4,430,148 issued to Schaefer on Feb. 7, 1984; U.S. Pat. No. 4,560,427 issued to Flood on Dec. 24, 1985 entitled "Ultrasonic Seal and Cut Method and Apparatus"; and U.S. Pat. No. 4,693,771 issued to Payet, et al. on Sep. 15, 1987 entitled "Woven Textile Fabric Having and Ultrasonically Cut and Sealed Edge and Apparatus and Process for Producing Same"; all of which references are incorporated herein by reference. U.S. Pat. No. 5,236,430 entitled "Disposable Training Pant Having Fusion-Slit Side Seams", issued to Russell Bridges on Aug. 17, 1993; and U.S. Pat. No. 3,457,132 issued to Tuma, et al. on Jul. 22, 1969 entitled "Apparatus for Severing and Sealing Webs of Heat Sealable Packaging Material in a Single Operation", disclose preferred methods and apparatus for severing and sealing webs using thermal energy and mechanical energy including ultrasound. These references are also incorporated herein by reference.

Figure 5:
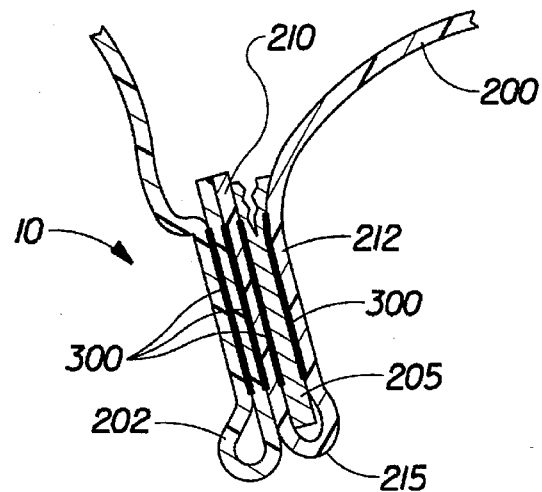
FIG. 5 is an enlarged cross-sectional view of an alternative embodiment of the seam area in the configuration in which the seam is fixed.
Figure 6:
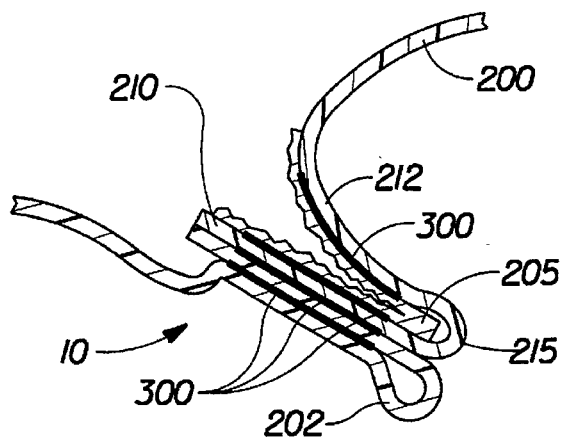
FIG. 6 is an enlarged cross-sectional view of the seam area shown in FIG. 5 in a partially open configuration.
Figure 7:
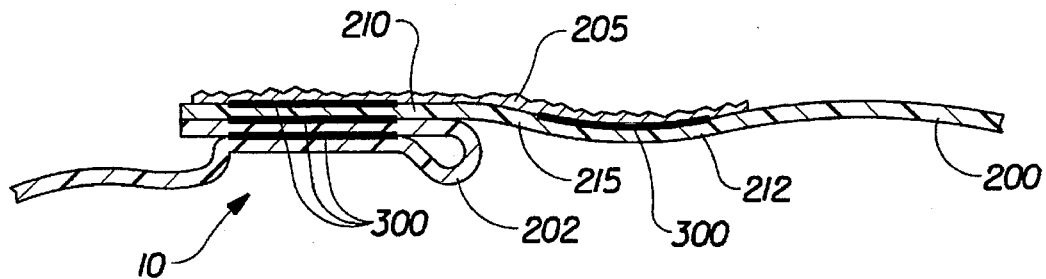
FIG. 7 is an enlarged cross-sectional view of the seam area shown in FIG. 5 in an open configuration.

An alternative embodiment of the present invention is shown in FIGS. 5–7. FIG. 5 shows the first and second members 200 and 202 of the present invention in a configuration after the first and second members 200 and 202 have been provided juxtaposed one another, the barrier member 205 has been provided, the first member 200 has been folded about the barrier member 205 and the joining means has been applied. In this embodiment, joining means 205 preferably joins not only the proximal portion 212 of the first member 200 with at least a portion of the second member, but also joins the barrier member 205 to both the proximal portion 212 and the distal portion 210 of the first member 200. Thus, as shown in FIGS. 5–7, to open the seam 10 to a flangeless configuration (FIG. 7), the barrier member 205 is preferably torn or separated. Although the structure of barrier member 205 itself is shown to be tearing or separating, the barrier member 205 could alternatively separate from either or both the proximal portion 212 or the distal portion 210. The force needed to open the seam will be dependent upon the forces needed to tear or separate the structure of the barrier member 205 or the force needed to separate the barrier member from either or both the proximal portion 212 or the distal portion 210. Thus, seams with different opening characteristics can be produced by the method of the present invention depending on the structural characteristics of the barrier member 205 or the joining means 300 chosen.

In one particularly preferred embodiment, the barrier member 205 comprises a nonwoven material that will tear with less force than is needed to separate the barrier member 205 from either the proximal portion 212 or the distal portion 210. Thus, a nonwoven material will be disposed along at least a portion of one surface of both the proximal portion 212 and the distal portion 210 of the first member 200. This configuration is especially preferred when the seam 10 is to be used in a disposable article such as the one shown in FIG. 8. The torn barrier member 205 provides a skin friendly surface that can be disposed against the skin of a wearer once the seam 10 is opened to its flangeless configuration (FIG. 7).

FIG. 8 shows one preferred embodiment of a disposable garment 15 comprising of the seam 10 formed by the method of the present invention. The seam 10 as shown in FIG. 8 is preferably formed by the method described above wherein the barrier member 205 is tearable or separable, and preferably comprises a skin friendly material. The barrier member 205 may span the entire length of the seam 10 or any portion of the seam 10. Thus, a seam 10 may be formed having an openable portion 500 and a closed portion 505. (As used herein, the term "openable portion" refers to that portion of the seam comprising a barrier member allowing the seam to be opened to a flangeless configuration. The term "closed portion" refers to that portion of a seam that has no barrier member, and thus may not be opened.) As shown in FIG. 8, the openable portion 500 of the seam 10 may be shorter in length than distance between the waist hoop 40 and the leg openings 44. This may give the user a greater fit range for a given size garment or may be used to help the user to tailor the fit of the garment to the particular wearer by allowing the user to open the seam 10 when desired to provide a particular size or fit.

Figure 10:
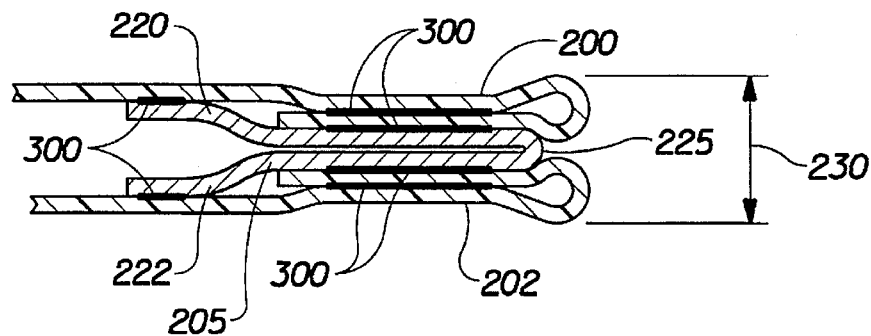
FIG. 10 is an enlarged cross-sectional view of an alternative embodiment of the seam area in the configuration in which the seam is fixed.
Figure 11:
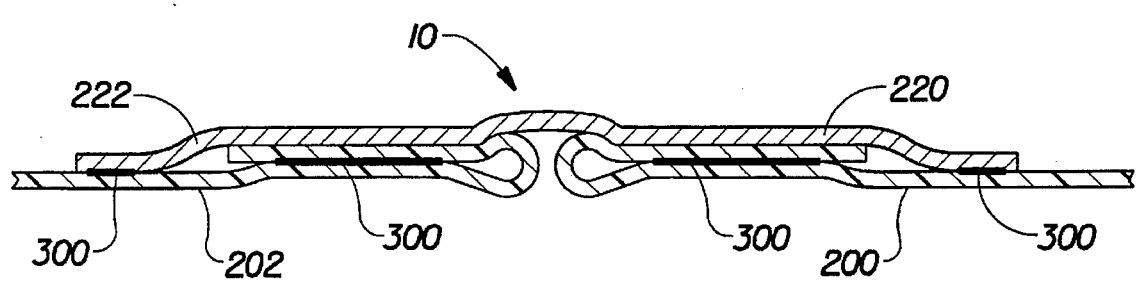
FIG. 11 is an enlarged cross-sectional view of the seam area shown in FIG. 10 in an open configuration.

An alternative embodiment of the present invention is shown in FIGS. 10 and 11. FIG. 10 shows the elements used to form the seam 10 of the present invention in a seaming configuration (As used herein, the term "seaming configuration" refers to a configuration in which the elements of the seam 10 may positioned with regard to each other and joined to form the seam 10.) FIG. 11 shows the seam 10 of the present invention in an open configuration. (As used herein, the term "open configuration" refers to the configuration of the elements comprised in the seam 10 after they have been opened or placed in a configuration in which the seam 10 is likely to be used, such as in a diaper that has been placed on a wearer.)

As shown in FIGS. 10 and 11, the seam 10 comprises a first member 200 and a second member 202. First and second members 200 and 202 may comprise a single fold as shown in FIGS. 10 and 11, multiple folds or no folds at all. Further, the first member 200 and the second member 202 may comprise any material as described above or known in the art that is suitable for use in disposable articles such as training pants 20 which may be joined together to form seam 10.

A barrier member 205, having a first portion 220 and a second portion 222 preferably separated by fold 225, is disposed between at least a part of the first member 200 and at least a part of the second member 202. (In an alternative embodiment, the barrier member 205 may comprise a separable material that is pulled apart, as described above with regard to the separable barrier member shown in FIGS. 5–7, when the seam 10 is manipulated into its open configuration.) In preferred embodiments, the first portion 220 of the barrier member 205 is juxtaposed at least a part of the first member 200 and the second portion 222 of the barrier member 205 is juxtaposed at least a part of the second member 202. In this preferred configuration, as shown in FIG. 10, a laminate 230 is formed comprising at least a part of the first member 200, at least a part of the second member 202 and at least a part of the barrier member 205 between the first and second members 200 and 202.

The barrier member 205 may comprise any known material or means that will prevent the first and second portions 220 and 222 of the barrier member 205 from becoming completely or unseparably joined when the seam 10 is formed. (Examples of suitable barrier members are described above with regard to other embodiments of the present invention.) The barrier member 205 may be a separate element joined to the first member 200, the second member 202 or both. Alternatively, the barrier member 205 may comprise an dement or material that is unitary or integrate with at least a portion of the first member 200, the second member 202 or both, such as a nonwoven material that has been laminated to either the first member 200, the second member 202 or both. Other examples of barrier members 205 that could be unitary or integral with the first or second members 200 and 202 may comprise materials that have been chemically, mechanically or otherwise manipulated in predetermined regions to act as a barrier to the joining means 300 used to form the seam 10. Further still, the barrier member 205 may comprise an extensible or elastomeric member so as to provide stretch in the region of the seam when the disposable article is worn.

The flangeless seam 10 of the present invention further comprises a joining means 300. The joining means 300 is disposed across at least part of the laminate 230 such that at least part of the first portion 220 of the barrier member 205 is joined with at least a part of the first member 200 and at least a part of the second portion 222 of the barrier member 205 is joined with at least part of the second member 202. Preferably, the first portion 220 of the barrier member 205 and the second portion 222 of the barrier member 205 are not joined. (However, the first portion 220 and the second portion 222 may be separably joined.) Thus, the unjoined (or separable) first and second portions 220 and 222 may be separated to provide the seam in its open configuration, one example of which is shown in FIG. 11.

The joining means 300 of the present invention may comprise any suitable joining means known in the art. Suitable joining means include, but are not limited to, adhesives, pressure bonding means, heat bonding means, heat and pressure bonding means, ultrasound bonding means, infrared bonding means or any other joining means or combination of joining means known in the art. Other examples of suitable joining means 300 are described above with regard to other embodiments of the present invention.

Preferred Methods of Making a Flangeless Seams

It should be noted that the scope of the present invention is not intended to be limited by the particular order in which the steps of the method are described. For example, although the side notches 10 are shown to be removed in FIG. 9D, it is contemplated that the side notches 10 may be removed before, after or during any other step of the process. Further, the method of the present invention can be performed on-line in conjunction with, or at separate time and/or in a location remote from, the manufacture of the absorbent article which comprise the seams formed by the present method. If the process is performed on-line in conjunction with the manufacture of the absorbent article, the seams may be formed before, after or at the same time that the first and second members 200 and 202 are joined with the chassis 14 of the disposable article 15. Also, it should be understood that the exact size and shape of any member comprised in the disposable article 15, as well as the materials comprised in the members may vary depending on the desired characteristics of the disposable article 15.

Figure 9C:
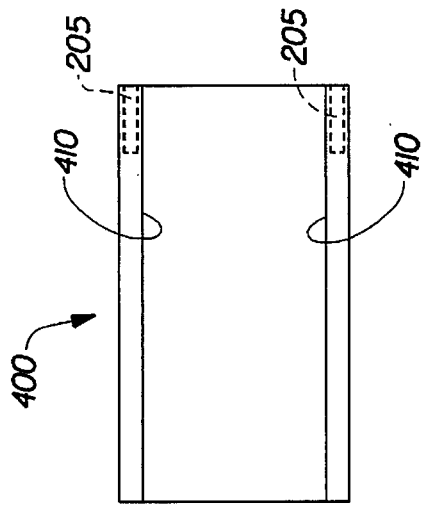
FIGS. 9A–G are schematic views of a parts of one method for making the seams of the present invention.
Figure 9B:
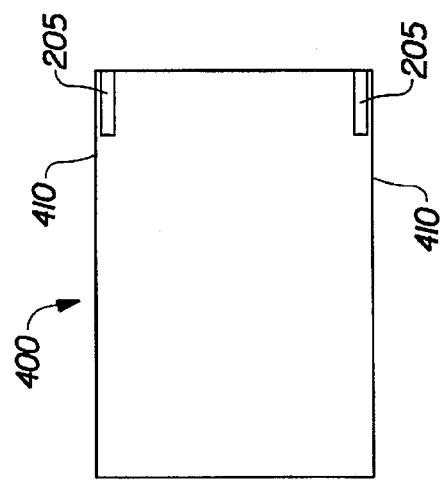
Figure 9A:
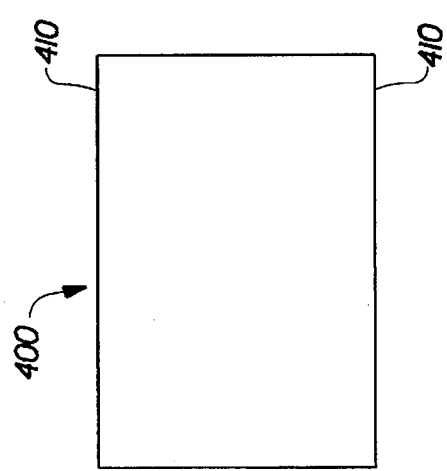
Figure 9G:
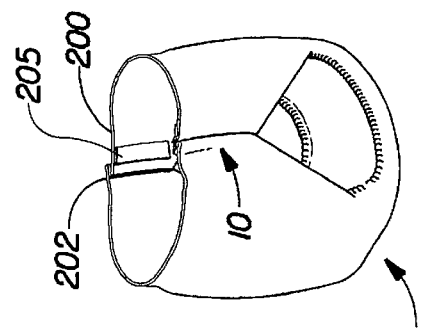
Figure 9F:
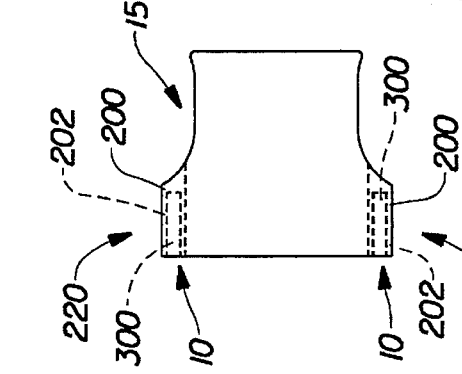
Figure 9E:
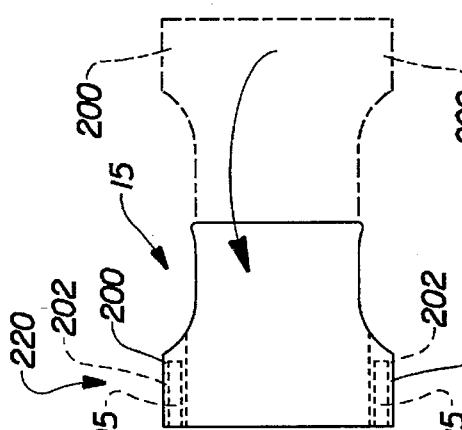
Figure 9D:
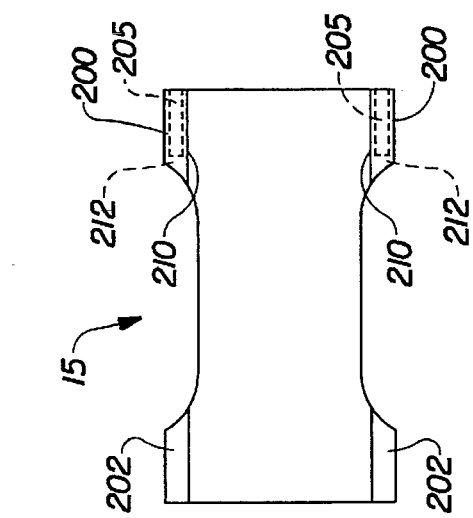

One preferred method for making the flangeless seams of the present invention is shown schematically in FIGS. 9A–G. The step depicted in FIG. 9A shows providing a web 400 having longitudinal side edged 410 that will be processed into disposable article 15 having first members 200 and second members 202. FIG. 9B shows barrier member 205 provided juxtaposed at least a portion of each longitudinal side edge 410. FIG. 9C shows the longitudinal side edges 410 being folded over the web 400. FIG. 9D shows the chassis 14 of the disposable article 15 with the side notches 10 removed. First member 200 is folded about the barrier member 205 providing opposing proximal and distal portions 212 and 210. The barrier member 205 is preferably disposed at least partially between the opposing proximal and distal portions 212 and 210. (The "proximal portion" 212 is that portion of the first member 200 which is joined, or will be joined, either directly or indirectly, to a portion of the disposable article 15, preferably other than the second member 202. The "distal portion" 210 is that portion of the first member 200 comprising the free end 214 which is generally not joined to any portion of the disposable article other than the second member 202 before the flangeless seam 10 is created.) FIG. 9E shows the second member 202 of the disposable article 15 being provided juxtaposed at least a portion of the first member 200 forming a laminate 220 of the first member 200, the second member 202 and the barrier member 205. (A more detailed drawing of the laminate 220 is shown in FIG. 3) FIG. 9F shows a joining means 300 being applied across at least a portion of laminate 220, the joining means 300 joining at least a portion of the first member 200 and the second member 202 to form a seam 10. The barrier member 205 prevents the joining means 300 from joining the opposing proximal and distal portions 212 and 210. Thus, the seam 10 may be opened from the configuration in which it is sealed (one embodiment is shown in FIG. 3) to a flangeless configuration wherein opposing proximal and distal portions 212 and 210 of the first member 200 are in a relatively planar configuration with regard to one another (The planar configuration is shown in FIG. 9G and in more detail in FIG. 4).

In one preferred embodiment of the present invention, the first step of the method for manufacturing a flangeless seam includes providing a first member 200. The method of the present invention further comprises the step of providing a barrier member 205, as shown in FIGS. 3–7. The means by which the barrier member 205 may be provided, as well as the timing and location for providing the barrier member 205 will be dependent on the exact barrier member 205 chosen. However, once a particular barrier member 205 has been chosen, the barrier member 205 may be provided by any suitable means known in the art. The means by which the barrier member 205 may be provided, as well the timing and location for providing the barrier member 205 will be dependent on the exact barrier member 205 chosen. However, once a particular barrier member 205 has been chosen, the barrier member 205 may be provided by any suitable means known in the art.

In one preferred embodiment, as shown in FIG. 9C, once the barrier member 205 is provided, the longitudinal side edges 10 are folded over the barrier member 205. (As stated above, the exact order of the steps of the process are not critical, thus, the barrier member 205 may be provided before or after the longitudinal side edges 10 are folded.)

The method for making the seam of the present invention further comprises the step of providing a second member 202. The second member 202 is preferably provided juxtaposed at least a portion of the first member 200 at a location wherein the proximal and distal opposing portions 212 and 210 have the barrier member 205 disposed between them. This forms a laminate 220 (one embodiment of which is shown in FIG. 3) including the proximal and distal opposing portions 212 and 210, and the barrier member 205. (As used herein, the term "laminate" refers to any number of materials that are in a generally overlapping configuration so as to form at least two layers. The materials included in the laminate may comprise single layer materials or laminates of similar or different materials. Further, any laminates comprised in the laminate 220 may have layers that are joined or unjoined with each other.)

Once the materials comprised in the laminate 220 have been properly configured, the seam 10 is formed. The seam 10 comprises those portions of the laminate 220 that are joined together (i.e. at least a portion of the first member 200 and at least a portion of the second member 202). To form the seam 10, a joining means 300 is applied across at least a portion of the laminate 220. In one preferred embodiment, the joining means 300 is applied across the seam area 250 as shown in FIG. 3. The joining means 300 joins at least a portion of the first member 200 and at least a portion of the second member 202. However, the barrier member 205 prevents the joining means 300 from joining at least a portion of the proximal portion 212 with the distal portion 210. Thus, a flangeless seam 10 is formed that may be opened to the relatively planar configuration shown in FIG. 4.

An alternative preferred method of making the embodiment of the flangeless seams of the present invention depicted in FIGS. 10–11 is shown schematically in FIGS. 12A–G. The step depicted in FIG. 12A shows providing a web 400 having longitudinal side edges 410 that may be processed into absorbent article 15 having first members 200 and second members 202. FIG. 12B shows the longitudinal side edged 410 being folded over the web 400. FIG. 12C shows barrier member 205 being provided juxtaposed at least a portion each longitudinal side edge 410. FIG. 12D shows the chassis 14 of the disposable article 15 with the side notches 10 removed. FIG. 12E shows the second member 202 being provided juxtaposed at least a portion of the barrier member 205 forming a laminate 230 of the first member 200, the barrier member 205 and the second member 202. (A more detailed drawing as of one embodiment of the laminate 230 is shown in FIG. 10.) FIG. 12F shows a joining means 300 being applied across at least a portion of the laminate 230 joining at least a portion of the barrier member 300 to each first and second member 200 and 202 to form a seam 10. The barrier member 205 prevents at least a portion of the first member 200 and at least a portion of the second member 202 from becoming directly joined to each other. Thus, the seam 10 may be opened from the configuration in which it was sealed (one embodiment is shown in FIG. 10) to a flangeless configuration wherein the first and second members 200 and 202 are in a relatively planar configuration with regard to one another. (An example of the seam in a planar configuration is shown in FIG. 12G, and more detailed in FIG. 11.)

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A flangeless seam for joining front and rear portions of a disposable article, the seam comprising:
   a first member;
   a second member, at least a portion of the second member overlapping at least a portion of the first member;
   a barrier member disposed between at least a portion of the overlapping portions of the first member and the second member forming a laminate having a seam area; and
   a joining means disposed in at least a portion of the seam area joining at least a portion of the first member to at least a portion of the second member, the barrier member preventing at least a portion of the first member from becoming joined with at least a portion second member.

2. A flangeless seam for joining front and rear portions of a disposable article having an open configuration and a seaming configuration, the seam comprising:
   a first member having a first proximal portion and a first distal portion, the first distal portion folded upon at least a portion of the first proximal portion to provide a common interface between the first distal portion and the first proximal portion when the seam is in the seaming configuration;
   a second member having a second proximal portion and a second distal portion, the first distal portion and the second distal portion being joinable to one another;
   a barrier member disposed between at least a part of the common interface forming a laminate of at least a part of the first proximal portion, at least a part of the first distal portion, at least part of the second distal portion and at least a part of the barrier member when the seam is in the seaming configuration; and
   a joining means spanning at least a portion of the laminate when the seam is in the seaming configuration, the joining means joining at least a part of the first distal portion and at least a part of the second distal portion, the barrier member preventing the joining means from joining at least a part of the common interface of the first proximal portion and the first distal portion such that the unjoined parts of the first proximal portion and the first distal portion may be separated to provide the seam in its open configuration.

3. The flangeless seam of claim 2 wherein the barrier member comprises a release agent applied to at least a portion of the common interface.

4. The flangeless seam of claim 2 wherein the barrier member is separably joined to the first member, the second member, or both, such that the first and second members can be pulled apart to provide the flangeless seam in its open configuration.

5. The flangeless seam of claim 2 wherein the barrier comprises a member that may be removed after the joining means is applied.

6. The flangeless seam of claims 1 or 2 wherein the barrier member is integral with at least a portion of the second member.

7. A flangeless seam for joining front and rear portions of a disposable article having an open configuration and a seam configuration, the seam comprising:
   a first member;
   a second member;
   a barrier member having a first portion and a second portion separated by a fold, the first portion of the barrier member being juxtaposed with at least a part of the first member and the second portion of the barrier member being juxtaposed at least a part of the second member forming a laminate; and
   a joining means disposed across at least a part of the laminate, at least a part of the first portion of the barrier member being joined with at least a part of the first member and at least a part of the second portion of the barrier member being joined with at least a part of the second member, wherein the first portion of the barrier member and second portion of the barrier member are not joined such that the unjoined first and second portions may be separated to provide the seam in its open configuration.

8. The flangeless seam of claims 1, 2 or 7 wherein the first member comprises a fold.

9. The flangeless seam of claims 2 or 7 wherein the first member comprises more than one fold.

10. The flangeless seam of claims 2 or 7 wherein the second member comprises a fold.

11. The flangeless seam of claims 1, 2 or 7 wherein the barrier member comprises a separable material.

12. The flangeless seam of claims 1, 2 or 7 wherein the joining means consists of any of the bonding means selected from the following group: pressure sensitive adhesive, heat, pressure, heat and pressure, ultrasound and hot melt adhesive.

13. The flangeless seam of claims 1, 2 or 7 wherein the barrier member consists of any of the barrier members selected from the following group: a nonwoven; a polymeric film; a laminate of nonwoven and a polymeric film; talc; silicone; and cotton.

14. A disposable article for wearing about the torso of a wearer, comprising:
   a chassis having a front portion, a rear portion, and a crotch portion disposed between flangeless portion and the rear portion; and
   the flangeless seam of claims 2 or 7 joining the front portion with the rear portion to form at least one leg opening.

15. The disposable article of claim 14 comprising a pair of flangeless seams joining the front portion with the rear portion to form two leg openings and a waist opening.

16. The disposable article of claim 14 wherein the chassis comprises a topsheet, a backsheet and an absorbent core disposed between the topsheet and the backsheet.

17. The disposable article of claim 14 wherein the chassis further comprises a pair of laterally opposed longitudinal side regions, each of the side regions comprising a first member disposed in the waist portion and a second member disposed in the rear portion.

18. The disposable article of claim 14 wherein the flangeless seam joins the first member with the second member.

19. The disposable article of claim 15 wherein the barrier member comprised in the flangeless seam spans only part way between each leg opening and the waist opening.

20. The disposable article of claim 19 wherein the barrier member comprises a separable material such that the portion of the flangeless seam comprising the barrier member may be pulled apart to an open configuration.

* * * * *

UNITED STATES PATENT AND TRADEMARK OFFICE
CERTIFICATE OF CORRECTION

PATENT NO. : 5,662,638
DATED : September 2, 1997
INVENTOR(S) : Larry Kenneth Johnson et al.

It is certified that error appears in the above-identified patent and that said Letters Patent is hereby corrected as shown below:

Column 1,
Line 11, "partities" should read -- panties --.

Column 2,
Line 50, "potion" should read -- portion --.

Column 6,
Line 54, "then" should read -- their --.

Column 10,
Line 64, "potion" should read -- portion --.
Line 67, "potion" should read -- portion --.

Column 11,
Line 3, "potion" should read -- portion --.
Line 7, "potions" should read -- potions --.
Line 13, "potion" should read -- portion --.

Column 12,
Line 64, "tom" should read -- torn --.

Column 13,
Line 31, "dosed" should read -- closed --.
Line 35, "dosed" should read -- closed --.

Column 14,
Line 25, "dement" should read -- element --.

UNITED STATES PATENT AND TRADEMARK OFFICE
CERTIFICATE OF CORRECTION

PATENT NO. : 5,662,638
DATED : September 2, 1997
INVENTOR(S) : Larry Kenneth Johnson et al.

It is certified that error appears in the above-identified patent and that said Letters Patent is hereby corrected as shown below:

Column 18,
Line 40, "flangeless" should read -- the front --.

Signed and Sealed this

Eleventh Day of December, 2001

*Attest:*

*Attesting Officer*

NICHOLAS P. GODICI
*Acting Director of the United States Patent and Trademark Office*